United States Patent [19]

Nakamura

[11] Patent Number: 5,812,301
[45] Date of Patent: Sep. 22, 1998

[54] STAND FOR OPTICAL DEVICES

[75] Inventor: Katsushige Nakamura, Hachioji, Japan

[73] Assignee: Mitaka Kohki Co., Ltd., Tokyo, Japan

[21] Appl. No.: 381,918

[22] PCT Filed: Jun. 15, 1993

[86] PCT No.: PCT/JP93/00803

§ 371 Date: Feb. 13, 1995

§ 102(e) Date: Feb. 13, 1995

[87] PCT Pub. No.: WO94/28815

PCT Pub. Date: Dec. 22, 1994

[51] Int. Cl.$^6$ .............................. G02B 21/00; F16L 3/00
[52] U.S. Cl. ...................... 359/384; 359/382; 248/123.1
[58] Field of Search ................................. 359/368, 377, 359/381–384, 430; 248/123.1, 280.1, 542

[56] References Cited

U.S. PATENT DOCUMENTS

| | | | |
|---|---|---|---|
| 4,339,100 | 7/1982 | Heller et al. | 248/123.1 |
| 4,741,607 | 5/1988 | Heller | 359/384 |
| 5,173,802 | 12/1992 | Heller | 359/384 |
| 5,186,422 | 2/1993 | Nakamura | 359/382 |
| 5,205,522 | 4/1993 | Nakamura | 248/123.1 |
| 5,528,417 | 6/1996 | Nakamura | 359/384 |

OTHER PUBLICATIONS

English language abstracts of Japanese Patent Appln. Nos. JP–A3–253810 dated Nov. 12, 1991, JP–A2–257945 dated Oct. 18, 1990 & JP–A1–91847 dated Apr. 11, 1989.

Primary Examiner—Thong Nguyen
Attorney, Agent, or Firm—Michael D. Bednarek; Kilpatrick Stockton LLP

[57] ABSTRACT

Disclosed is a stand for optical devices, wherein both the vertical length of a second parallel link 3 and the lateral length of weight-retaining arm 19 are retractable, whereby a counterweight $W_4$ is moveable along a straight line X connecting the extremity of a supporting arm 9 and a rotational fulcrum S. Moving the counterweight $W_4$ along the straight line X provides an easy and secured balance adjustment of the weight of operating microscope, etc. $W_{1-3}$ both in horizontal and vertical directions.

6 Claims, 7 Drawing Sheets

STAND FOR OPTICAL DEVICES

FIELD OF THE INVENTION

This invention relates to a stand in which heavy medical optical devices such as operating microscope and its auxiliary devices are supported with a retaining link mechanism utilizing a parallel link and are balanced with a counterweight, and above-described operating microscope etc. can be retained or kept at the desired spatial positions during microsurgery.

DESCRIPTION OF THE PRIOR ART

In the fields of encephalotomy and cardiosurgery, a technique of so-called microsurgery is employed, in which surgeries are performed under observation of the focuses using operating microscopes as "medical optical devices". Various types of stand apparatuses, for retaining heavy operating microscope and its auxiliary devices at any desired spatial positions, to be utilized in such microsurgeries have been proposed (e.g. Japanese Patent Publication before Examination No. 32110/1981). These stands generally are of a balancing structure, in which a retaining link mechanism employing a parallel link is pivotally (tiltably) supported at an intermediary portion on a frame, and an operating microscope is supported at one end portion of the retaining link mechanism with a counterweight for countervailing the weight of the operating microscope being supported on the other end portion of the retaining link mechanism relative to the pivot thereof.

As a position where the balancing type stand is set up, an optimum position in an operating room is selected depending on the content of the surgery to be carried out, and balance is adjusted at the selected position. In other words, while the optimum position around the operating table is specified by a doctor prior to surgery, the doctor himself is in a sterilized region, so that moving the stand to the position to set up is carried out by an assistant such as a nurse who does not participate in the surgery. Since auxiliary devices such as a side microscope for assistant doctors and a video camera are attached to the operating microscope, the position of the counterweight is changed corresponding to the weight of these devices to adjust the entire balance of the stand.

However, moving such heavy counterweight is a tremendous task and is also dangerous for the nurse who is in most cases a woman. Further, the balance adjusting operation takes too much time to be advantageously rendered for emergent surgery and the like.

What is most serious in the prior art stand is that the balance adjustment between the operating microscope and the counterweight is very difficult due to the structure of the stand itself. More specifically, in order to stop the operating microscope and the auxiliary devices at the desired spatial positions, the operating microscope must be perfectly balanced in the horizontal and vertical directions. However, the prior art stand does not always have a structure which facilitates secured balance adjustment in the horizontal and vertical directions in accordance with the weight on the operating microscope side which changes depending on the presence or absence of various auxiliary devices.

This invention has been accomplished noting such prior art technique and is directed to provide a stand for optical devices which enables easy and secured balance adjustment in accordance with the weight change on the operating microscope side.

DISCLOSURE OF THE INVENTION

In the stand for optical devices according to the present invention, the intermediary portion of the retaining link mechanism essentially consisting of first and second parallel links which interlock each other is supported at a rotational fulcrum of a frame, medical optical device and/or its auxiliary devices are retained at the extremity of a supporting arm which is formed by laterally extending a part of the above described first parallel link, a counterweight is retained at the extremity of a weight-retaining arm which is formed by extending a part of the above described second parallel link in a lateral direction opposite to the extending direction of the above described supporting arm, and the counterweight is so provided that it is moveable on a straight line which connects the extremity of the above described supporting arm and rotational fulcrum, by making both the vertical length of the second parallel link and the lateral length of the weight-retaining arm retractable.

The counterweight which is moveable on the straight line connecting the extremity of the supporting arm and the rotational fulcrum enables easy and secured balance adjustment of the weight of the above described operating microscope side both in horizontal and vertical directions by the movement of the counterweight along the straight line even when the weight of the operating microscope side changes because of the presence or absence of the auxiliary devices.

Alternatively, a displacement detecting means which detects unbalance of the retaining link mechanism may be provided at a part of the retaining link mechanism so that the counterweight can be moved manually in response to the signal from the displacement detecting means.

Furthermore, a drive means which moves the counterweight by means of a motor may be provided to control the drive means in response to the signal from the displacement detecting means, thereby the counterweight can be automatically moved to positions where the counterweight and the operating microscope side are balanced.

BEST MODE FOR CARRYING OUT THE INVENTION

A preferred embodiment of this invention will be described below referring to the attached drawings. It should be noted here that the following description is made assuming that the arrow A and the arrow B shown in FIG. 1 mean the front side and the rear side, respectively.

The stand according to the preferred embodiment of the invention has a basic structure wherein a retaining link mechanism 4 essentially consisting of a first parallel link 2 and a second parallel link 3 is supported at a part (intermediary portion 4a) on a rotational fulcrum S on a frame 1, and an operating microscope $W_1$ and other devices are supported at one end portion (connecting point $\beta_1$) of a supporting arm 9 which is an extended portion of the first parallel link 2, while a counterweight $W_4$ is provided on the extremity of the weight-retaining arm 19 which is formed by extending a part of the above described second parallel link 3.

The base affixed with the reference number 5 has on the bottom a plurality of casters 6 with locking mechanisms, thus the entire stand is allowed to run on the floor. A frame 1 having a substantially rectangular U-shaped side profile is mounted on the base 5. The frame 1 is designed to be pivotable on the vertical axis $\alpha_1$ and also to be unpivotably locked by an electromagnetic clutch $C_1$ provided on the axis $\alpha_1$.

A first parallel link 2 is pivotably supported on the rotational fulcrum S assumed on the upper front end side of the frame 1. The first parallel link 2 is formed by combining a pair of first parallel vertical arms 7a,7b and a pair of first parallel horizontal arms 8a,8b. The front first vertical arm 7a of the first parallel link 2 is supported at the intermediary portion 4a on the rotational fulcrum S, as described above. An electromagnetic clutch $C_2$ is provided on the rotational fulcrum S, so that the front first vertical arm 7a can be locked at a desired pivoted position (i.e. the displaced state of the first parallel link 2). The upper portion of the front first vertical arm 7a supported on the rotational fulcrum S is bulged backward so as not to interfere with the body of a doctor who performs the surgery.

The upper first horizontal arm 8a of the first parallel link 2 extends forward to form a supporting arm 9 integrally therewith, and a vertical front arm 10 is pivotally attached to the connecting point $\beta_1$, at the front end portion thereof. The supporting arm 9 is also bulged upward so as not to interfere with the head of the doctor.

A supporting parallel link 11 consisting of two parallel links which interlock with each other is provided below the front arm 10 to be pivotable on the vertical axis $\alpha_2$. An electromagnetic clutch $C_3$ is provided at the upper end of the supporting parallel link 11, and an operating microscope (medical optical device) $W_1$ which is pivotable on the axis $\alpha_3$ is attached via another electromagnetic clutch $C_4$ to the lowermost portion of the supporting parallel link 11. The supporting parallel link 11 as a whole presents a curved shape, so that the doctor can operate the operating microscope $W_1$ easily. The view angle of the operating microscope $W_1$ can be changed by transforming the supporting parallel link 11. Incidentally, the transformed state of the supporting parallel link 11 can be locked by an electromagnetic clutch $C_5$. "Auxiliary devices" such as a side microscope $W_2$ for assistant doctors and a video camera $W_3$ for recording are attached to the operating microscope $W_1$. The weight on the operating microscope (WI) side changes by attaching or detaching these auxiliary devices.

A bell crank 12 is pivotably supported on the connecting points $\beta_3$ which is the origin of the supporting arm 9, and the rear end portion 12a of the bell crank 12 is connected via a vertical subarm 13 to the connecting point, $\beta_4$ of the frame 1, while the upper end 12b of the bell crank 12 is connected via a horizontal subarm 14 to the upper end portion 10a of the front arm 10. In other words, on the connecting point $\beta_3$ which is the origin of the supporting arm 9 is supported the bell crank 12, having the rear end portion 12a on the horizontal line including the connecting point $\beta_3$ and the upper end portion 12b on the perpendicular line including the connecting point $\beta_3$ the rear end portion 12a of the bell crank 12 and the connecting point $\beta_4$ of the frame 1 are connected by the vertical subarm 13, which is parallel with the first vertical arm 7a and has a length which is equal to the linear distance from the connecting point $\beta_3$ of the first vertical arm 7a to the rotational fulcrum S; and the upper end portion 12b of the bell crank 12 and the upper end portion 10a of the front arm 10 are connected by the horizontal subarm 14 which is parallel with the supporting arm 9 and has a length which is equal to that of the supporting arm 9.

With the aid of the vertical subarm 13 and the horizontal subarm 14 additionally provided, a "parallel link" is formed by the rotational fulcrum S $\Rightarrow$ connecting point $\beta_3$ $\Rightarrow$ rear end portion 12a $\Rightarrow$ connecting point $\beta_4$; while another "parallel link" is formed by the connecting points $\beta_3$ $\Rightarrow$ connecting point $\beta_1$ $\Rightarrow$ upper end portion 10a $\Rightarrow$ upper end portion 12b. Accordingly, since the bell crank 12 cannot be turned no matter how the first parallel link 2 is transformed, the front arm 10 is constantly maintained in the vertical posture, and consequently the axis $\alpha_2$ of the supporting parallel link 11 is prevented from tilting to maintain constantly the vertical posture.

Next, there provided below the first parallel link 2 the second parallel link 3 which deforms interlockedly with the first parallel link 2. The second parallel link 3 has an upper second horizontal arm 17a as formed with a lower first horizontal arm 8b of the first parallel link 2 backwardly extended, which pivotally supports a front second vertical arm 16a as formed with the rear first vertical arm 7b downwardly extended, and a rear second vertical arm 16b as parallel and equal in length with the front second vertical arm 16a. The pivotally supported on the respective bottom end of the front and rear second vertical arms 16a,16b is a plate arm 18 of which portion between the second vertical arms 16a,16b is a lower second horizontal arm 17b, and behind the arm 17b is the weight-retaining arm 19. Thus, the second parallel link 3 comprises upper and lower second horizontal arms 17a,17b, and front and rear second vertical arms 16a,16b.

In the second parallel link 3, the front and rear second vertical arms 16a,16b are retractable, so that the lengths thereof are adjustable. More specifically, the arms 16a,16b comprises cylindrical sliding arms 20 and base arms 21 to be inserted into the sliding arms 20, and flexible spiral bars 22 respectively provided within the base arms 21 are spirally received by receiving parts 23 within the sliding arms 20. Accordingly the rotating directions of the spiral bars 22 vary the vertical lengths of the second vertical arms 16a,16b.

Incidentally, the weight-retaining arm 19 behind the plate arm 18 is also provided with cylindrical sliding arm 24 and base arm 37 to be inserted into the sliding arm 24. The provided under the sliding arm 24 is a receiving part 38 to which a spiral bar 39 rearwardly extended from the plate arm 18 is spirally received. Accordingly the rotating directions of the spiral bar 39 vary the length of the weight-retaining arm 19. At the end of the weight-retaining arm 19, the counterweight $W_4$ is provided. The counterweight $W_4$ is positioned on the straight line X which connects the connecting point $\beta_1$ on the extremity of the supporting arm 9 and the rotational fulcrum S.

A motor M is provided on the lower end of the plate arm 18, and a spur gear 40 and bevel gear 41 are provided on the shaft of the motor M. The spur gear 40 engages with a spur gear 42 connected to the spiral bar 39 on the side of the weight-retaining arm 19. The bevel gear 41 engages with a spur gear 43 provided to the spiral bar 22 in the second vertical arm 16b. The spiral bars 22 in the second vertical arms 16a,16b are provided with a pulley 44, respectively, and the pullys 44 are engaged with a belt 45 for rotation. Accordingly, rotating the motor M in one direction rotates both the spiral bars 22,39 simultaneously, expanding the second vertical arms 16a,16b and weight-retaining arm 19. On the other hand, rotating the motor M in the opposite direction contracts the second vertical arms 16a,16b and weight-retaining arm 19. Thus, expansion and contraction of the second vertical arms 16a,16b and weight-retaining arm 19 move the counterweight $W_4$ on the straight line X. This is the most characteristic point in structure of the present invention. The motor M is controlled by a later-described control section D which is combined with the motor M to constitute a "drive means".

Figure 10:
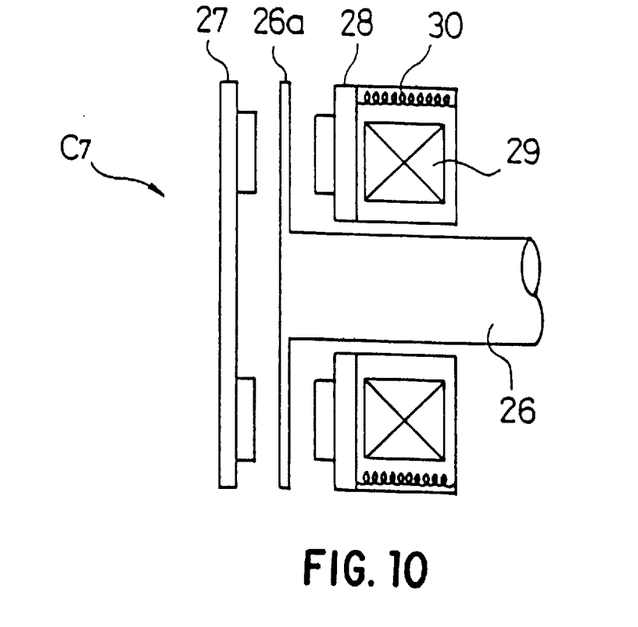
FIG. 10 is a cross-sectional view showing an electromagnetic clutch is in an unlocked state.

Next, a detection lever 25 is provided on the left side (reverse side of the first front vertical arm 7a in FIG. 1) of the connecting point $\beta_5$ where the front first vertical arm 7a and the lower horizontal arm 8b are connected. While a conventional electromagnetic clutch $C_6$ is disposed on the right side of the connecting point $\beta_5$, the detection lever 25 is attached to another electromagnetic clutch $C_7$ disposed to a connecting shaft 26 penetrating the lower first horizontal arm 8b ("which is a counterpart member") through the front first vertical arm 7a. More specifically, a disc-shaped flange 26a is formed at one end of the connecting shaft 26, and the electromagnetic clutch $C_7$ is provided with a fixed flange 27 and a movable flange 28. The flange 26a is grasped and locked between the fixed flange 27 and the movable flange 28. The movable flange 28 side is provided with an electromagnetic coil 29 on which the movable flange 28 is magnetically adsorbed and a spring 30 which urges the movable flange 28 toward the fixed flange 27. Accordingly, the electromagnetic coil 29 attracts the movable flange 28 overcoming the force of the spring 30 during energization, so that the detection lever 25 assumes a state of free rotation with respect to the connecting shaft 26 (see FIG.10).

Figure 11:
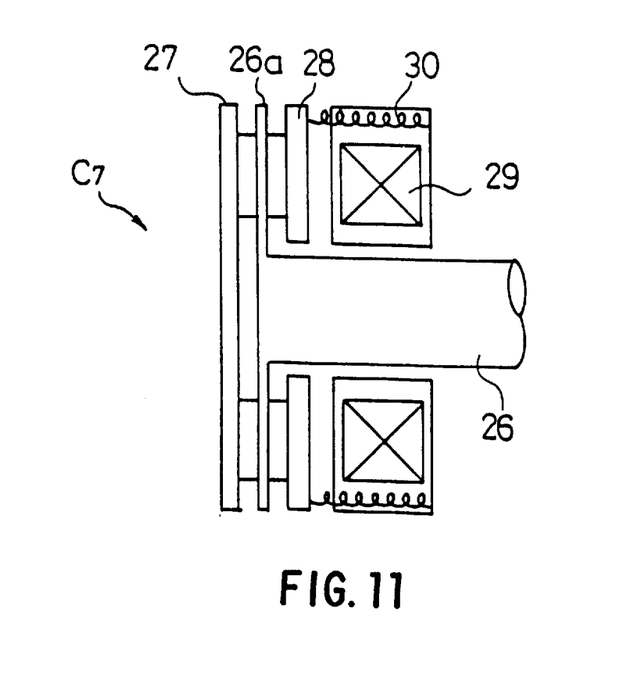
FIG. 11 is a cross-sectional view showing an electromagnetic clutch is in a locked state.

However, the attraction by the electromagnetic coil 29 is not exerted during de-energization, so that the movable flange 28 is pushed toward the fixed flange 27 to hold the flange 26a of the connecting shaft 26 between the fixed flange 27 and the movable flange 28, and thus the detection lever 25 can be turned integrally with the connecting shaft 26 (see FIG. 11).

A metal shaft 31 is disposed to protrude from the first vertical arm 7a at a position opposing to the detection lever 25, and the outer end portion of the shaft 31 is resiliently supported by a resilient bushing 32 disposed in the middle of the detection lever 25. An irradiation section 33 for irradiating a beam f is provided on the first vertical arm 7a at a position opposing to the upper end portion of the detection lever 25. The irradiation section 33 contains a light-emitting diode 34 therein, and the beam f from the light-emitting diode 34 is designed to pass through a slit 35 and impinge upon the upper end portion of the detection lever 25. The upper end portion of the detection lever 25 to be irradiated with the beam f is provided with a two-piece photo-location section 36 having two sensors 36a,36b. Accordingly, so long as the detection lever 25 is maintaining a vertical neutral position relative to the first vertical arm 7a, the beam f transmitted through the slit 35 impinges at the middle of the two sensors 36a,36b, and thus the sensors 36a,36b receive the beam f on the same area, producing no output difference. However, if the detection lever 25 is pivoted to either side and deviated from the neutral position, the photo-detecting area in the sensor 36a or 36b locating on the side opposite to the side the detection lever 25 is shifted is increased to generate an output difference, thus enabling detection of the shift. The photo-location section 36 is electrically connected to the control section D, and the control section D allows the motor M to be driven based on the signal from the photo-location section 36, whereby the counterweight $W_4$ can be moved in a direction such that the detection lever 25 can resume the neutral position. The detection lever 25, the irradiation section 33, the photo-location section 36, etc. constitute the "displacement detection means".

In the meantime, the operational procedures of the stand apparatus will now be described. First, the entire stand apparatus is carried to a position near the operating table specified by a doctor. A specified side microscope $W_2$ and a video camera $W_3$ are attached to the operating microscope $W_1$. At this point, the weight of the counterweights $W_4$ and the weight on the operating microscope ($W_1$) side including the side microscope $W_2$ and the video camera $W_3$ (hereinafter referred to as "operating microscope, etc. $W_{1-3}$") are not necessarily balanced. Incidentally, the retaining link mechanism 4 itself from which the counterweights $W_4$ and the operating microscope, etc. $W_{1-3}$ are detached is balanced on the rotational fulcrum S.

Figure 1:
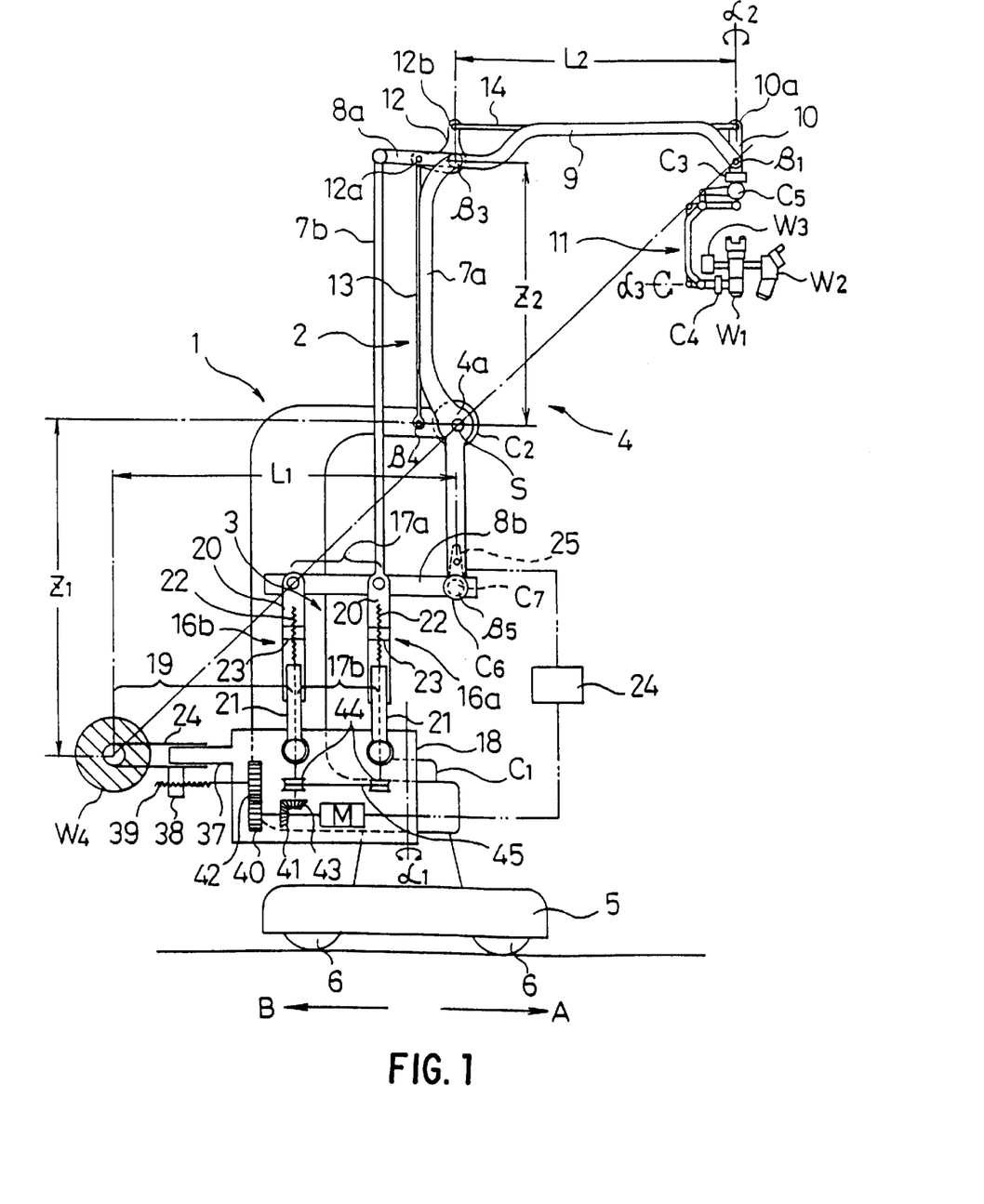
FIG. 1 is an entire side view showing a stand according to this invention.

Subsequently, the retaining link mechanism 4 is once allowed to resume the standard posture as shown in FIG. 1, and the electromagnetic clutch $C_7$ is actuated to immobilize the detection lever 25 onto the connecting shaft 26 of the lower first horizontal arm 8b. If the weight of the operating microscope, etc. $W_{1-3}$ and that of the counterweights $W_4$ in this state is not balanced, the angle of the front first vertical arm 7a is inevitably changed with respect to the lower first horizontal arm 8b which is a "counterpart member", so that the detection lever 25 locked integrally with the connecting shaft 26 of the lower first horizontal arm 8b is pivoted or shifted relative to the vertical arm 7a.

Since the detection lever 25 and the first vertical arm 7a constitute via the resilient bushing 32 a resilient supporting structure, the detection lever 25 has an allowance of being shifted within the maximum elastic deformation range of the resilient bushing 32. When the detection lever 25 is shifted relative to the first vertical arm 7a, the light receiving area receiving the beam f from the irradiation section 33 in the sensor 36a or 36b locating on the side opposite to the direction the detection lever 25 is shifted is increased to cause an output difference in the photo-location section 36, and thus the direction that the detection lever 25 is shifted, i.e. the change in the angle of the first vertical arm 7a with respect to the lower first horizontal arm 8b which is a "counterpart member" at the connecting point, $\beta_5$ can be found.

Figure 2:
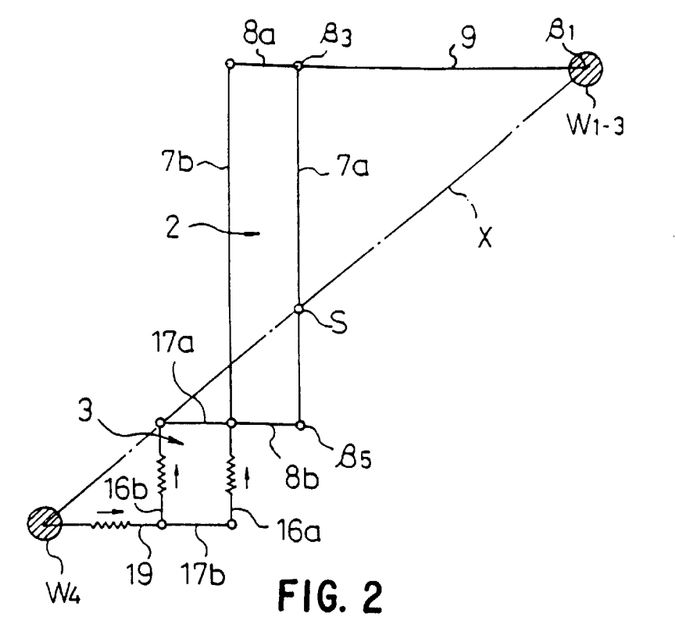
FIG. 2 is a schematic view showing a stand in which both the vertical length of a second parallel link and the lateral length of a weight-retaining arm are in a retracted state.
Figure 3:
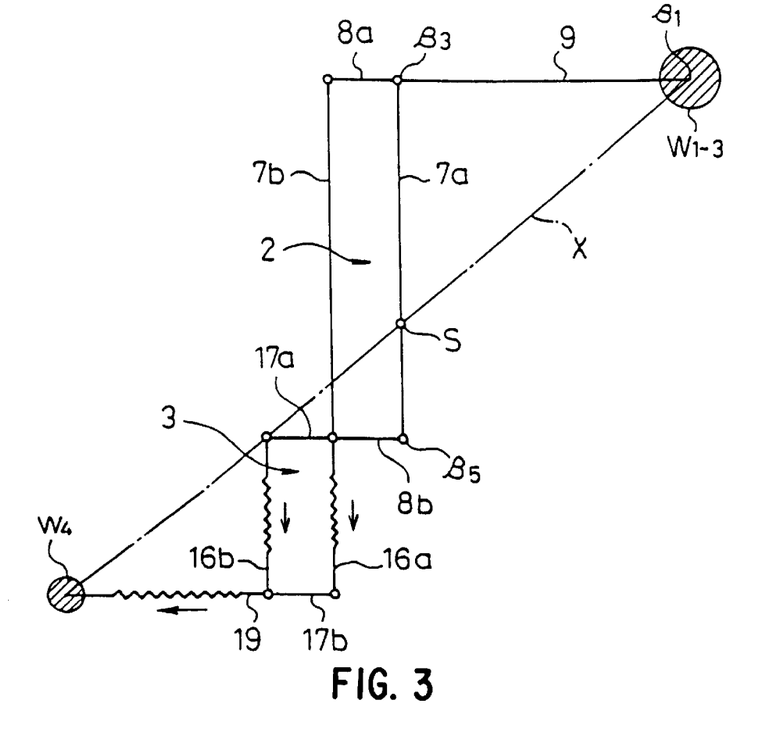
FIG. 3 is a schematic view showing a stand in which both the vertical length of the second parallel link and the lateral length of the weight-retaining arm are in a extended state.

Accordingly, the control section D, upon receipt of a signal from the photo-location section 36, decides the rotational direction of the motor M to vary the lengths of the second vertical arms 16a,16b and weight-retaining arm 19 in the direction and in an amount necessary to correct the displacement of the detection lever 25, move the counterweight $W_4$, whereby the counterweight $W_4$ is moved in directions along the straight line X. In other words, if the weight of the operating microscope, etc. $W_{1-3}$ is small, the counterweight $W_4$ is moved in a direction towards the operating microscope, etc. $W_{1-3}$ (see FIG. 2); whereas if the weight of the operating microscope, etc. $W_{1-3}$ is large, the counterweight $W_4$ is moved in a direction away from the operating microscope, etc. $W_{1-3}$ (see FIG. 3).

Thus, the reason why the weight of the operating microscope, etc. $W_{1-3}$ side can be balanced only by moving the counterweight $W_4$ in directions along the straight line X will be described below. In such type of stand, the weight of the operating microscope, etc. $W_{1-31}$ and that of the counterweight $W_4$ must be balanced in the horizontal and vertical directions on the rotational fulcrum S. Namely, to describe referring to FIG. 1, while the weight of the operating microscope, etc. $W_{1-3}$ and the weight of the counterweight $W_4$ must satisfy the following relationship:

* Balance in the vertical direction:

$$W_{1-3} \times Z_2 = W_4 \times Z_1$$

* Balance in the horizontal direction:

$$W_{1-3} \times L_2 = W_4 \times L_1$$

In this invention, all the connecting point $\beta_1$ rotational fulcrum S, and counterweight $W_4$ are on the straight line X and the counterweight $W_4$ moves only along the straight line X, so that the weight of the operating microscope $W_1$ side and the counterweight $W_4$ are well balanced both in the vertical and horizontal directions only by moving the counterweight $W_4$ along the straight line X even when the weight of the operating microscope, etc. $W_{1-3}$ side changes.

That is to say, the operating microscope, etc. $W_{1-3}$ which are positioned $Z_2$: $L_2$ with respect to the rotational fulcrum S necessitate the counterweight $W_4$ to be moved at the ratio of $Z_2$: $L_2$ in accordance with the weight change of the operating microscope, etc. $W_{1-3}$ if any. However in this invention, since the position of the counterweight $W_4$ to the rotational fulcrum S, i.e. $Z_1$: $L_1$ is equal to the above described $Z_2$: $L_2$ as seen from the positional relationship according to the straight line X as a reference, the weights of the operating microscope, etc. $W_{1-3}$ and the counterweight $W_4$ can be balanced only by moving the counterweight $W_4$ along the straight line X even when the weight of the operating microscope, etc. $W_{1-3}$ changes because of the presence or absence of the auxiliary devices.

Figure 4:
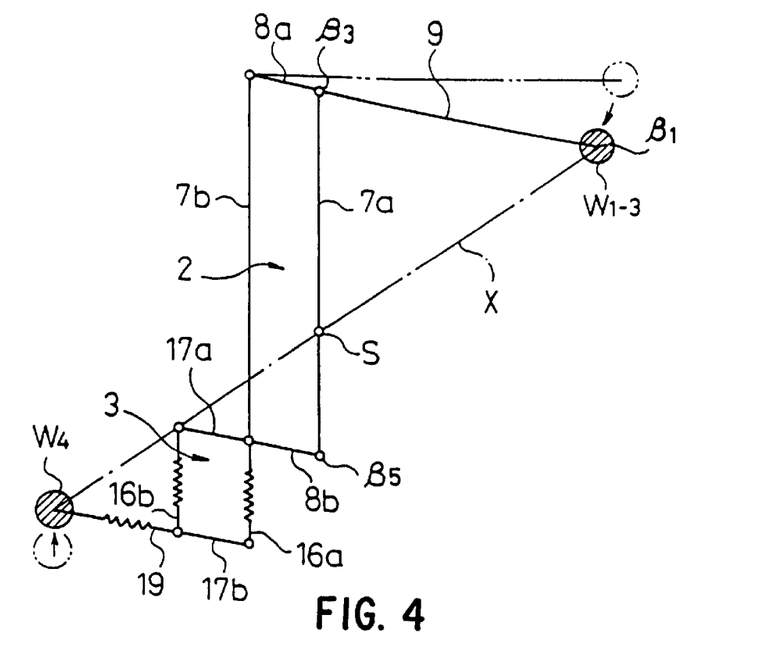
FIG. 4 is a schematic view showing a vertical displacement in the stand in FIG. 2.
Figure 5:
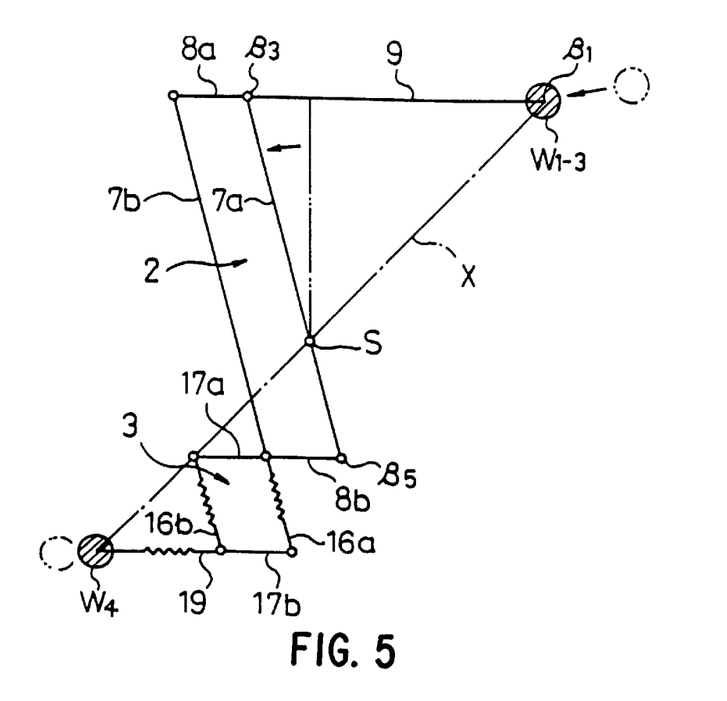
FIG. 5 is a schematic view showing a horizontal displacement in the stand in FIG. 2.
Figure 6:
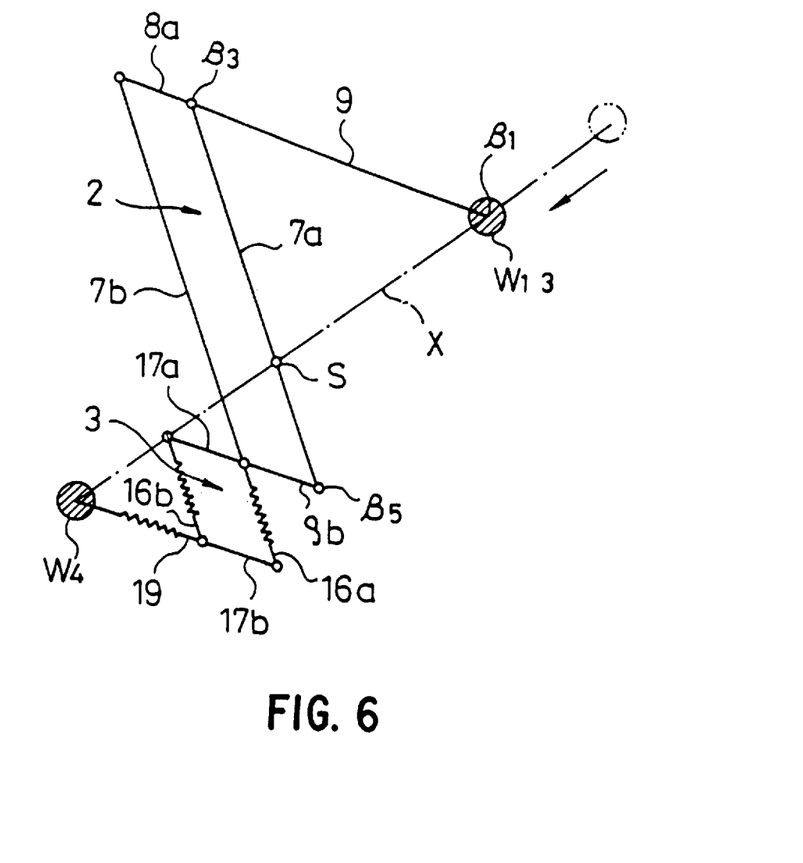
FIG. 6 is a schematic view showing vertical and horizontal displacement in the stand in FIG. 2.
Figure 7:
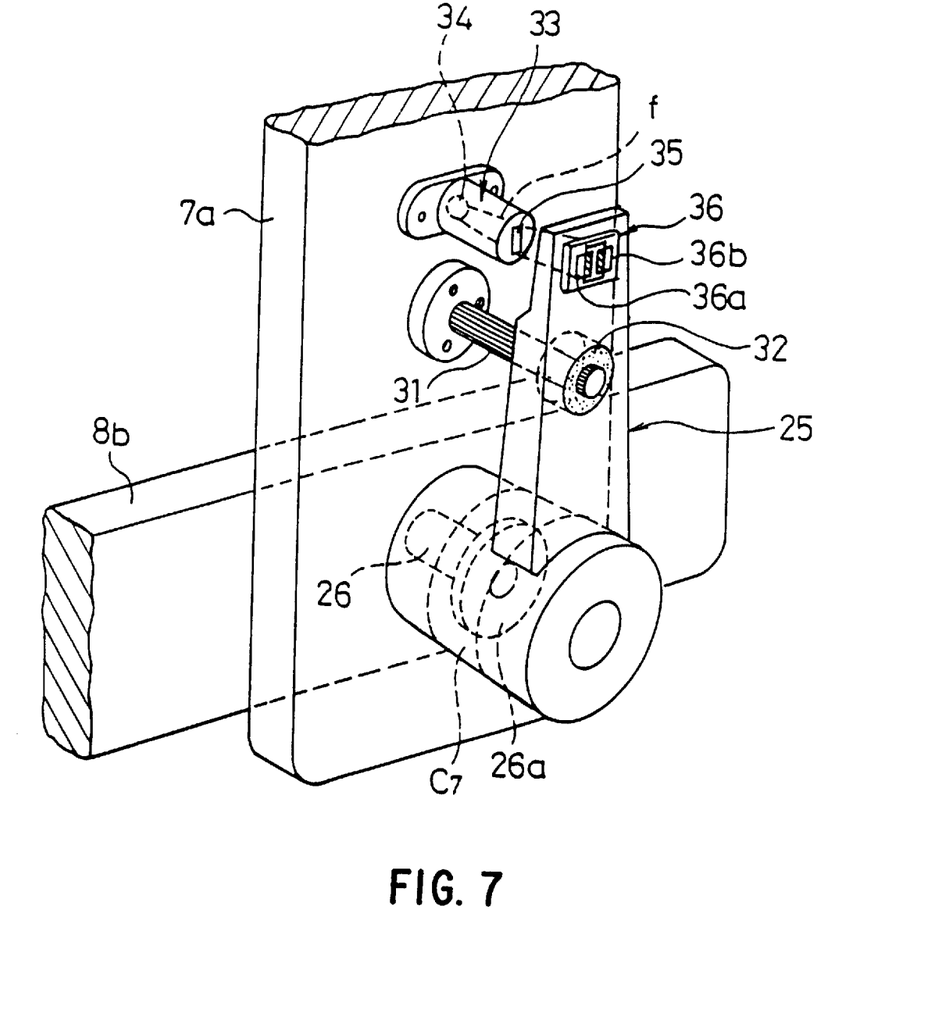
FIG. 7 is a perspective view showing a displacement detecting means.
Figure 8:
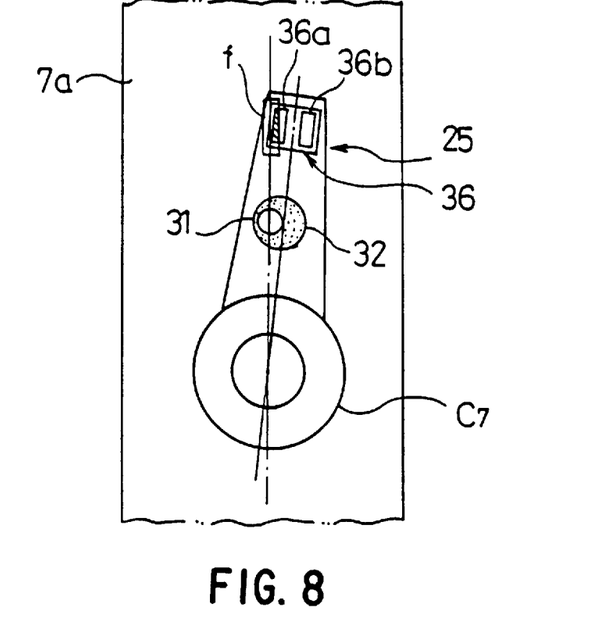
FIG. 8 is a side view showing a detection lever which is shifted to one side.
Figure 9:
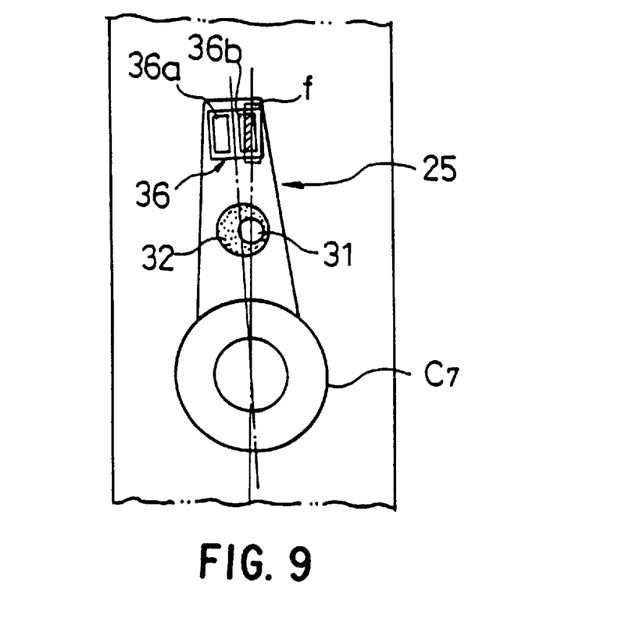
FIG. 9 is a side view showing a detection lever which is shifted to the other side.

Therefore, when the counterweight $W_4$ is moved to a balancing point, the displacement of the detection lever 25 is corrected to allow the detection lever 25 to resume the neutral position, so that the photo-location section 36 detects the state of the neutral position, and the control section D stops driving of the motor M to allow the counterweight $W_4$ to stop at the balancing point. Now that the weight of the operating microscope, etc. $W_{1-3}$ and that of the counterweight $W_4$ is balanced, the electromagnetic clutch $C_7$ of the detection lever 25 is deactuated to provide a free joint at the connecting point $\beta_5$ connecting the first vertical arm 7a and the lower first horizontal arm 8b. In the balanced stand, when the operating microscope, etc. $W_{1-3}$ are vertically moved as shown in FIG. 4, horizontally moved as shown in FIG. 5, or in a vertically-and-horizontally-combined direction as shown in FIG. 6, the balance between the operating microscope, etc. $W_{1-3}$ and the counterweight $W_4$ is maintained, thereby the operating microscope, etc. $W_{1-3}$ can be positioned at any desired spatial position.

Meanwhile, the bell crank 12, the vertical subarm 13, the horizontal subarm 14 and the front arm 10 disposed in the embodiment described above constitute a structure where the supporting parallel link 11 for supporting the operating microscope, etc. $W_{1-3}$ can constantly maintain the vertical posture, even if the operating microscope, etc. $W_{1-3}$ are moved in the horizontal and vertical directions. In this regard also, the structure of the embodiment facilitates the balancing operation.

Further, while the frame 1 described in the above embodiment is of a floor type which is set on the floor, the frame 1 may be of a ceiling type which is suspended from the ceiling of the operating room.

Meanwhile, the technique of detecting displacement of the retaining link mechanism 4 may not be limited to the embodiment utilizing the detection lever 25 as described above, and other means such as rotary encoders can be utilized. Further, the position where the displacement is detected may not be limited to the connecting point $\beta_5$.

In addition, the "auxiliary devices" may not be limited to the side microscope $W_2$ and video camera $W_3$, and other devices can be attached.

INDUSTRIAL APPLICABILITY

As described above, in the stand for optical devices according to this invention, the changes in the vertical length of the second parallel link and the lateral length of the weight-retaining arm, and movements of the counterweight along a predetermined straight line allow easy and secured balance adjustment between the weight of the operating microscope and auxiliary devices and that of the counterweight both vertically and horizontally, so that the stand is particularly suitable for retaining optical devices for medical use which require a short-time balance adjustment in an operation room.

What is claimed is:

1. A stand for optical devices, comprising:
  a frame, the frame including a rotational fulcrum;
  a retaining link mechanism including a first linkage and a second linkage, the second linkage having an adjustable height, said retaining link mechanism being supported at an intermediate portion of said first linkage at the rotational fulcrum of said frame, wherein said first linkage includes a supporting arm extending transversely therefrom and being constructed and arranged to support an optical device, wherein said second linkage includes a weight-retaining arm extending transversely therefrom in a direction opposite to said supporting arm, the weight-retaining arm having an adjustable length;
  a counterweight provided at extremity of said weight-retaining arm;
  means for adjusting the height of the second linkage; and
  means for adjusting the length of the weight-retaining arm, such that the height of said second linkage and the length of said weight-retaining arm are variable, and means for moving the counterweight in correspondence with a variance in said height of said second linkage and in said length of said weight-retaining arm so as to remain on a straight line which connects a distal extremity of said supporting arm and said rotational fulcrum.

2. The stand for optical devices according to claim 1, wherein said first and second linkages collectively comprise substantially parallel first, second, and third horizontal arms and substantially parallel first, second, and third vertical arms,
  wherein said first linkage includes said first and second vertical arms, said first and second vertical arms having corresponding first ends that are each pivotably connected to said first horizontal arm, wherein said first vertical arm is pivotably connected at an intermediate portion thereof to said frame at said rotational fulcrum and is pivotably connected at a second end thereof opposite said first end to said second horizontal arm;

wherein said second vertical arm is pivotably connected at an intermediate portion thereof to an intermediate portion of said second horizontal arm and is pivotably connected at a second end thereof opposite said first end to an end of said third horizontal arm; and wherein said third vertical arm is pivotably connected at a first end thereof to an end of said second horizontal arm opposite said end of said second horizontal arm to which said first vertical arm is pivotably connected and is pivotably connected at a second end thereof to an end of said third horizontal arm opposite said end of said third horizontal arm to which said second vertical arm is pivotably connected; and means for adjusting the length of the second and third vertical arms, wherein the length of said second and third vertical arms is variable.

3. The arm for optical devices according to claim 2, further comprising a third parallel linkage including a vertical arm portion, said third linkage being provided on a distal end of said supporting arm to support an optical device thereon.

4. The stand for optical devices according to claim 3, further comprising means for detecting an angular displacement between one of said first and second vertical arms and one of said horizontal arms pivotably connected to said one of said first and second vertical arms, said angular displacement detection means being mounted on said second horizontal arm, said displacement detection means comprising:
 a detection lever pivotably supported on said second horizontal arm via an electromagnetic clutch in a locked or unlocked state,
 a shaft connecting said detection lever and said one of said first and second vertical arms and being resiliently supported at one end portion thereof by a resilient bushing,
 a beam irradiation section provided on one of said first and second vertical arms, and a photo-location section provided on the detection lever.

5. The stand for optical devices according claim 4, wherein the second and third vertical arms have vertical lengths further comprising:
 a drive means, comprising a motor, for changing both the vertical length of said second and third vertical arms and the lateral length of said weight-retaining arm, thereby allowing said counterweight to remain on said straight line, and
 a control section for controlling said motor in accordance with said signal from said photo-location section, such that said counterweight moves in a direction whereby said detection lever returns to a non-displaced position relative to said one of said first and second vertical arms.

6. The stand for optical devices according claim 5, further comprising a bell crank pivotably supported on said first vertical arm substantially at the location from which said supporting arm extends, said bell crank having a rear end portion substantially collinear with said first horizontal arm and an upper end portion on a vertical line including said location from which said supporting arm extends from said first vertical arm, said supporting arm being provided with a front link at a distal end thereof wherein said rear end portion of said bell crank and a portion on said frame are connected by a vertical subarm which is substantially parallel with said first vertical arm and has a length which is equal to a distance from said location on said first vertical arm from which said supporting arm extends to said rotational fulcrum of said first vertical arm, wherein said upper end portion of said bell crank and an upper end portion of said front link are connected by a horizontal subarm which is parallel with said supporting arm and has a length which is substantially equal to the distance of said supporting arm.

* * * * *